US00PP37100P2

(12) United States Plant Patent
Lim

(10) Patent No.: US PP37,100 P2
(45) Date of Patent: Nov. 18, 2025

(54) ***HIBISCUS* PLANT NAMED 'ALTbigbird'**

(50) Latin Name: *Hibiscus rosa-sinensis*
Varietal Denomination: ALTbigbird

(71) Applicant: Altman Specialty Plants llc, Vista, CA (US)

(72) Inventor: Peter Lim, Escondido, CA (US)

(73) Assignee: Altman Specialty Plants llc, Vista, CA (US)

( * ) Notice: Subject to any disclaimer, the term of this patent is extended or adjusted under 35 U.S.C. 154(b) by 0 days.

(21) Appl. No.: 19/022,369

(22) Filed: Jan. 15, 2025

(51) Int. Cl.
*A01H 5/02* (2018.01)
*A01H 6/60* (2018.01)

(52) U.S. Cl.
USPC ..... Plt./257

(58) Field of Classification Search
USPC ..... Plt./226, 257
See application file for complete search history.

(56) References Cited

U.S. PATENT DOCUMENTS

PP22,523 P3 * 2/2012 Dupont, Sr. ..... A01H 6/608 Plt./257

* cited by examiner

*Primary Examiner* — Karen M Redden

(57) ABSTRACT

A new and distinct cultivar of *Hibiscus* plant named 'ALTbigbird' is disclosed, characterized by large, rich yellow flowers with a deep red center that fades out to dark pink. Flowers have large, soft petals which overlap and open fully. Plants are compact and bushy, around 3 feet tall. Foliage is dark, dense and characteristically heart-shaped. The new variety is a *Hibiscus*, typically produced as an ornamental plant.

2 Drawing Sheets

Figure 1:
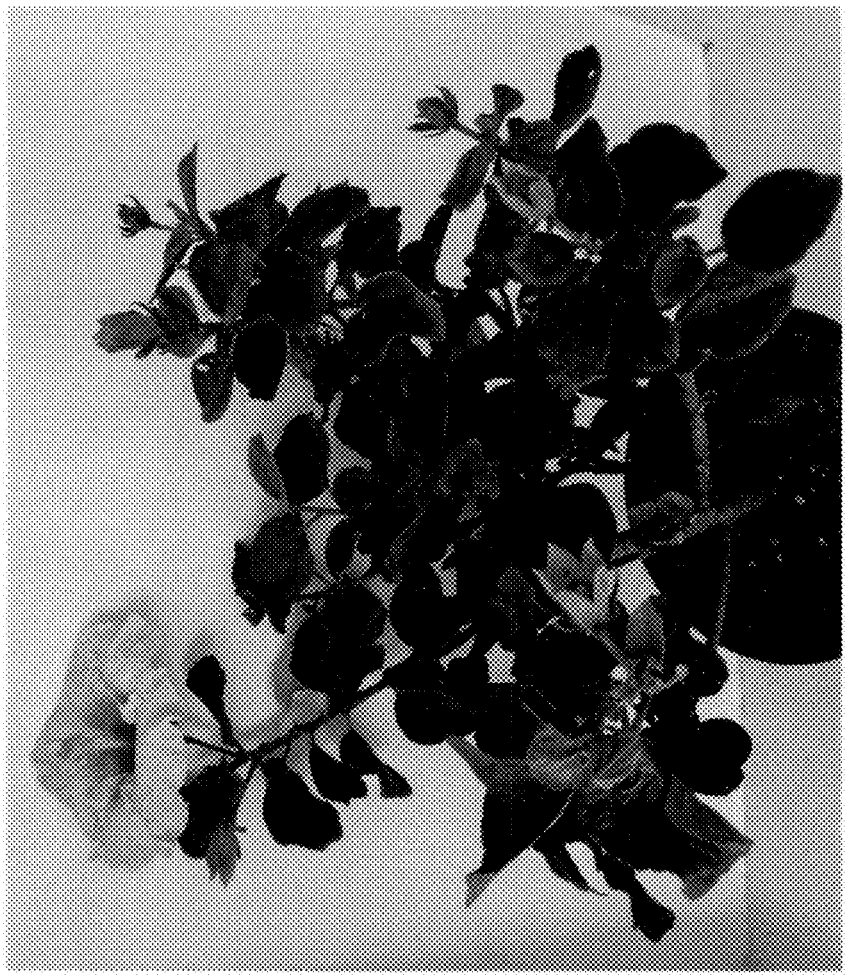

Latin name of the genus and species: *Hibiscus rosa-sinensis.*

Variety denomination: 'ALTbigbird'.

BACKGROUND OF THE INVENTION

The new *Hibiscus* cultivar is a product of a planned breeding program conducted by the inventor, Peter Lim. The objective of the breeding program was to produce vigorous *Hibiscus rosa-sinensis* cultivars with healthy foliage. The cross resulting in this new variety was made Aug. 22, 2016.

The seed parent is the unpatented *Hibiscus rosa-sinensis* 'Saffron', unpatented. The pollen parent is the unpatented variety *Hibiscus rosa-sinensis* 'Faith', unpatented. The new variety was identified and selected as a potentially interesting selection in 2019. Selection was made at a commercial nursery in Vista, California.

Asexual reproduction of the new cultivar 'ALTbigbird' was first performed in August of 2019 in Vista, California, by vegetative cuttings. Subsequent propagation has shown that the unique features of this cultivar are stable and reproduced true to type in successive generations.

SUMMARY OF THE INVENTION

The cultivar 'ALTbigbird' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'ALTbigbird'. These characteristics in combination distinguish 'ALTbigbird' as a new and distinct *Hibiscus* cultivar:

1. Large rich yellow flowers with a deep red center that fades out to dark pink.
2. Large, soft petals which overlap and open fully
3. Compact, bushy plant around 3 feet tall.
4. Dark, dense, large heart-shaped foliage.

PARENT COMPARISONS

Plants of the new cultivar 'ALTbigbird' are similar to the seed parent in most horticultural characteristics. However, characteristics of the new cultivar differ in the following:

1. Flowers of the new cultivar have large rich yellow flowers with a deep red center that fades out to dark pink; flowers of the seed parent are solid yellow.

Plants of the new cultivar 'ALTbigbird' are similar to the pollen parent in most horticultural characteristics. However, characteristics of the new cultivar differ in the following:

1. Flowers of the new cultivar have large rich yellow flowers with a deep red center that fades out to dark pink; flowers of the pollen parent are dark orange with a red center.

COMMERCIAL COMPARISON

Plants of 'ALTbigbird' are similar in some horticultural characteristics to the variety *Hibiscus* 'Heat Flash', unpatented. The new variety, however, differs in the following:

1. Flowers of 'ALTbigbird' are about 2.5 cm larger in diameter than flowers of 'Heat Flash'.
2. Plants of 'Heat Flash' are taller than plants of 'ALTbigbird'.
3. Petals of 'ALTbigbird' open more fully than petals of 'Heat Flash'.

4. Petals of 'ALTbirdbird' are moderately ruffled and rugose, petals of 'Heat Flash' are very deeply ruffled and rugose.

Plants of 'ALTbigbird' are similar in some horticultural characteristics to the variety *Hibiscus* 'Hula Girl', unpatented. The new variety, however, differs in the following:

1. Flowers of 'ALTbigbird' are about 2.5 cm larger in diameter than flowers of 'Hula Girl'.
2. Plants of 'Hula Girl' are much larger than plants of 'ALTbigbird'.
3. Plants of 'ALTbigbird' are denser and bushier than plants of 'Hula Girl'.

BRIEF DESCRIPTION OF THE PHOTOGRAPHS

The accompanying photograph in FIG. 1 illustrates in full color a plant of 'ALTbigbird' grown outdoors at a commercial nursery in Vista, California. This plant is about 1.5 years old and grown in a 2-gallon pot.

Figure 2:
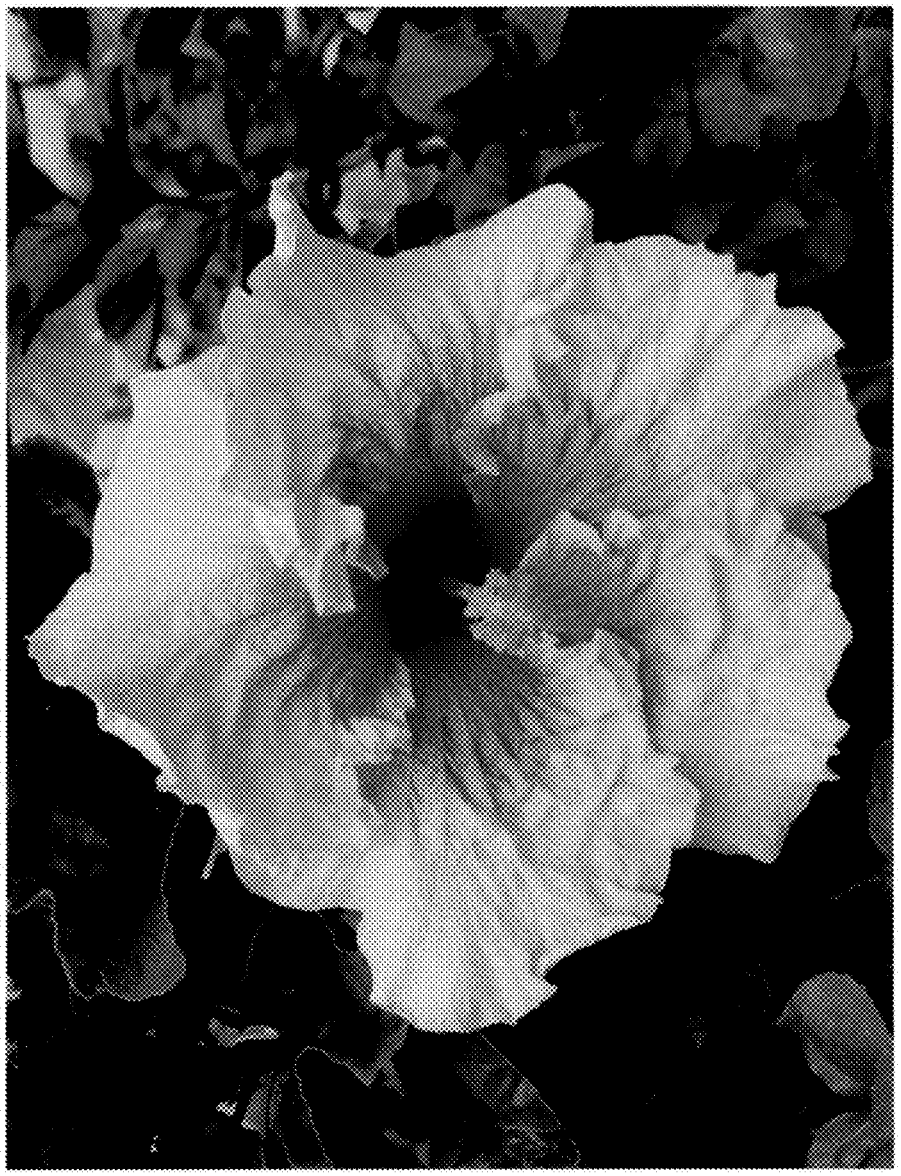

FIG. 2 is a close-up view of a typical flower of 'ALTbigbird'.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015, except where general terms of ordinary dictionary significance are used. The following observations and measurements describe a 'ALTbigbird' plant. This plant was grown at a commercial nursery in Vista, California. The growing temperature ranged from about 7° C. to 30° C. during the day and from about 5° C. to 12° C. during the night. No artificial light, photoperiodic treatments were given to the plants. Measurements and numerical values represent averages of typical plant types.

Botanical classification: *Hibiscus rosa-sinensis* 'ALTbigbird'.

PROPAGATION

Typical method: Hardwood stem cuttings.

Root description: Roots are fine, fibrous and well branched. Tan/brown in color, not effectively measured with a color chart.

PLANT

Plant type: Tender, woody flowering shrub.

Age of plant described: Approximately 1.5 years old.

Growth habit: Compact.

Height: 45 cm. 100 cm at maturity.

Plant spread: 50 cm. approximately 100 cm at maturity.

Branching characteristics: 2 to 4 breaks from a pinch, occurring at an average 45° angle.

Length of primary lateral branches: 20 to 60 cm.

Quantity of lateral branches: Each primary lateral branch has 6 to 10 laterals.

Characteristics of primary lateral branches:

*Diameter.*—Average range 14 to 20 mm.

*Color.*—New growth RHS Green 143A, Mature growth RHS Greyed-Green 197B, striated Grey-Brown N199A.

*Texture.*—New growth very sparsely hirsute, older growth striated.

Internode length: Average 3 cm.

FOLIAGE

Leaf:

*Arrangement.*—Alternate.

*Quantity.*—Average 12 to 20 per branch.

*Leaf internode.*—1 cm.

*Average length.*—8 to 10 cm, excluding petiole.

*Average width.*—8 cm.

*Shape of blade.*—Cordate.

*Apex.*—Acute.

*Base.*—Obtuse.

*Margin.*—Entire or irregularly and shallowly crenate.

*Aspect.*—Strongly undulating.

*Texture of top surface.*—Glabrous.

*Texture of bottom surface.*—Sparse and very short hirsute.

*Color.*—Young foliage upper side: RHS Green 139A. Young foliage under side: RHS Green 137A. Mature foliage upper side: RHS Green 139A. Mature foliage under side: RHS Green 137B.

*Venation.*—Type: Pinnate. Venation color, upper side: RHS Green 137B. Venation color, under side: RHS Green 138B.

*Petiole.*—Length: 1.8 to 2.5 cm. Diameter: 4 to 5 mm. Color: Near RHS Green 143C, maturing to Greyed-Green 191B completely flushed Greyed-Purple N187A. Texture: Densely short hirsute.

*Leaf stipule.*—Not observed.

FLOWER

Natural flowering season: Nearly year-round in Southern California.

Flower type and habit: Solitary, rotate.

*Single, double, multiplex.*—Single.

*Petals overlapping.*—Strongly overlapping.

Quantity of flowers: A plant of about 2 years old has approximately 30 open flowers at one time during Summer.

Rate of flower opening: 4 to 6 days from bud to fully opened flower.

Flower longevity on plant: 1 to 2 days.

Persistent or self-cleaning: Self-cleaning.

Bud:

*Shape.*—Ovate.

*Length.*—6 cm.

*Diameter.*—2.1 cm.

*Color.*—RHS Green-Yellow 1C, apex, lightly flushed Yellow-Green 145A.

Flower size:

*Diameter.*—16 to 20 cm.

*Depth.*—10 cm.

Petals:

*Quantity.*—5.

*Arrangement.*—Whorled, strongly overlapping.

*Length.*—11 cm.

*Width.*—9 cm.

*Shape.*—Slightly asymmetrical broad spatulate.

*Apex*.—Obtuse rounded with irregular, shallow crenations.
*Base*.—Attenuate.
*Margin*.—Entire. Moderate undulation.
*Texture*.—Glabrous all surfaces. Strongly rugose top and bottom.
*Color*.—When opening, upper surface: RHS Yellow 4A. Large basal blotch (forming flower eye) Red 53A changing to Red 53C and finally feathering out to 52A at outermost eye. When opening, lower surface: RHS Yellow 10B, basal area Yellow 10D. Fully opened, upper surface: RHS Yellow 6A. Large basal blotch (forming flower eye) Red 53A fading to Red 53C and finally 52A at outermost eye. Fully opened, lower surface: RHS Yellow 11A, basal area Yellow 11D. Thin marginal strip near base Red 53A. Ratio of basal blotch/eye to petal size: Overall 50% of petal blade is blotched. 40% solidly blotched, 20% feathered blotch. Feathering: Soft feathering from center blotch.

Sepals:
*Quantity*.—5.
*Length*.—2.5 cm.
*Width*.—1.2 cm.
*Shape*.—Oblanceolate.
*Margin*.—Entire.
*Apex*.—Acute.
*Base*.—Fused.
*Color*.—Upper surface: RHS Green 143C. Lower surface: RHS Yellow-Green 144A.
*Texture*.—Upper surface: Softly pubescent. Lower surface: Very short hirsute.

Epicalyx:
*Quantity of bracts*.—6.
*Bract length*.—1.5 cm to 1.9 cm.
*Bract width*.—3 to 4 mm.
*Bract shape*.—Straplike.
*Bract margin*.—Entire.
*Color*.—Upper surface: RHS Green 137A. Lower surface: Near RHS Green 137C.
*Texture*.—Upper surface glabrous, lower surface nonpubescent rough.

Peduncles:
*Length*.—2.5 to 3.3 cm.
*Diameter*.—4 to 5 mm.
*Angle*.—Approximately 45° to the lateral branch.
*Strength*.—Strong.
*Texture*.—Sparsely hirsute.
*Color*.—RHS Green 143A.

Fragrance: Faint musty scent.

REPRODUCTIVE ORGANS

Stamens:
*Number*.—About 50 to 60.
*Filament length*.—10 mm.
*Filament color*.—Near Yellow 8D.

Anthers:
*Shape*.—Irregular sphere.
*Length*.—About 3 mm.
*Color*.—Near RHS Yellow-Orange 14B.
*Pollen color*.—Near RHS Yellow-Orange 14B.
*Pollen amount*.—Scant.

Pistil:
*Number*.—1.
*Length*.—11 cm.
*Style*.—Length: 8 cm. Color: Lower section near Red 53A, mid-section has spiraling lines of 53A and Yellow 8D. Uppermost 1/3 Yellow 8D.
*Stigma*.—Shape: Peltate. Color: Near RHS Orange N25C. Ovary color: Near RHS Yellow 4D. Ovary length: 1.5 cm Ovary width: 8 mm.

OTHER CHARACTERISTICS

Seeds: Not observed.
Disease/pest resistance: Neither resistance nor susceptibility to normal diseases and pests of *Hibiscus rosa-sinensis* have been observed.
Temperature tolerance: USDA Zones 8 through 11.

What is claimed is:

1. A new and distinct cultivar of *Hibiscus* plant named 'ALTbigbird' as herein illustrated and described.

* * * * *